United States Patent
Cranor et al.

(10) Patent No.: US 9,090,821 B2
(45) Date of Patent: Jul. 28, 2015

(54) MIXED CATALYST SYSTEMS AND METHODS FOR CHEMILUMINESCENT REACTIONS

(71) Applicant: Cyalume Technologies, Inc., West Springfield, MA (US)

(72) Inventors: Earl Cranor, Longmeadow, MA (US); Linda Jacob, Woodbridge, CT (US); Patrick Taylor, Holyoke, MA (US)

(73) Assignee: Cyalume Technologies, Inc., West Springfield, MA (US)

( * ) Notice: Subject to any disclaimer, the term of this patent is extended or adjusted under 35 U.S.C. 154(b) by 0 days.

(21) Appl. No.: 14/294,014

(22) Filed: Jun. 2, 2014

(65) Prior Publication Data

US 2014/0353558 A1    Dec. 4, 2014

Related U.S. Application Data

(60) Provisional application No. 61/830,075, filed on Jun. 1, 2013, provisional application No. 61/830,071, filed on Jun. 1, 2013, provisional application No. 61/830,072, filed on Jun. 1, 2013, provisional application No. 61/830,070, filed on Jun. 1, 2013.

(51) Int. Cl.
  *C09K 11/07*    (2006.01)
  *C09K 11/02*    (2006.01)
  *G01N 21/76*    (2006.01)

(52) U.S. Cl.
  CPC ............... *C09K 11/07* (2013.01); *C09K 11/025* (2013.01); *G01N 21/76* (2013.01); *C09K 2211/1007* (2013.01); *C09K 2211/1018* (2013.01)

(58) Field of Classification Search
  CPC ....................................................... C09K 11/07
  USPC ............................................................ 252/700
  See application file for complete search history.

(56) References Cited

U.S. PATENT DOCUMENTS

| | | | |
|---|---|---|---|
| 2012/0097063 | A1 | 4/2012 | Cranor et al. |
| 2012/0126188 | A1 | 5/2012 | Schrimmer |
| 2014/0353559 | A1 | 12/2014 | Cranor et al. |
| 2014/0353560 | A1 | 12/2014 | Cranor et al. |
| 2014/0356975 | A1 | 12/2014 | Cranor et al. |

OTHER PUBLICATIONS

International Search Report and Written Opinion from International Application No. PCT/US2014/040573 dated Oct. 15, 2014.

*Primary Examiner* — Vu A Nguyen
(74) *Attorney, Agent, or Firm* — Greenberg Traurig, LLP (57) ABSTRACT

In some embodiments, the instant invention provides a chemiluminescent system, including: an activator system, including: (a) at least one first catalyst including at least one benzyl amine; (b) at least one second catalyst including at least one of: (i) a salicylate derivative, and (ii) a benzoate derivative; (c) at least one first solvent, and (d) at least one peroxide, where the at least one first catalyst is present in an amount ranging from 1 to 99 percent by weight of a combination of the at least one first catalyst and the at least one second catalyst; where the at least one second catalyst is present in an amount ranging from 99 to 1 percent by weight of the combination of the at least one first catalyst and the at least one second catalyst; and where the chemiluminescent system has at least one chemiluminescent property.

16 Claims, 4 Drawing Sheets

MIXED CATALYST SYSTEMS AND METHODS FOR CHEMILUMINESCENT REACTIONS

RELATED APPLICATIONS

This application claims the priority of U.S. provisional application Ser. No. 61/830,070, filed Jun. 1, 2013, entitled "BROAD TEMPERATURE PERFORMANCE CHEMILUMINESCENT SYSTEMS AND METHODS", Ser. No. 61/830,071, filed Jun. 1, 2013, entitled "LOW TEMPERATURE OXALATE SYSTEMS AND METHODS FOR CHEMILUMINESCENT REACTIONS", Ser. No. 61/830,072, filed Jun. 1, 2013, entitled "LOW TEMPERATURE ACTIVATOR SYSTEMS AND METHODS FOR CHEMILUMINESCENT REACTIONS", and Ser. No. 61/830,075, filed Jun. 1, 2013, entitled "MIXED CATALYST SYSTEMS AND METHODS FOR CHEMILUMINESCENT REACTIONS," which are incorporated herein by reference in their entireties for all purposes.

TECHNICAL FIELD

In some embodiments, the present invention relates to chemiluminescent systems and methods.

BACKGROUND

Chemiluminescence is the emission of light as a result of a chemical reaction. There may also be limited emission of heat during the chemical reaction. Typically, a reaction beginning with reactants A and B, with an excited intermediate, yields products and light. Typically, there are many applications that use chemiluminescence. For example, chemiluminescence is used in gas analysis, analysis of inorganic and/or organic species, detection and assay of biomolecules, DNA sequencing, lighting objects, and children's toys.

BRIEF SUMMARY OF INVENTION

In some embodiments, the instant invention provides a chemiluminescent system, including: an activator system, including: (a) at least one first catalyst including at least one benzyl amine; (b) at least one second catalyst including at least one of: (i) a salicylate derivative, and (ii) a benzoate derivative; (c) at least one first solvent, and (d) at least one peroxide, where the at least one first catalyst is present in an amount ranging from 1 to 99 percent by weight of a combination of the at least one first catalyst and the at least one second catalyst; where the at least one second catalyst is present in an amount ranging from 99 to 1 percent by weight of the combination of the at least one first catalyst and the at least one second catalyst; where a total concentration of the combination ranges from 0.002 to 25 percent by weight based on a total weight of the activator system; and where the chemiluminescent system has at least one chemiluminescent property.

In some embodiments, the instant invention further provides an oxalate system, providing: (a) at least one oxalate ester, (b) at least one second solvent, (c) at least one fluorescer, and (d) at least one inorganic salt, where a ratio of a weight of the oxalate system to a weight of the activator system ranges from 1:9 to 4:1.

In some embodiments, the at least one benzyl amine is selected from the group consisting of: dialkylbenzyl amines, alkyldibenzyl amines, tribenzyl amines, alkylarylbenzyl amines, and diarylbenzyl amines. In some embodiments, the amount of the at least one benzyl amine ranges from 10 to 0.001 percent by weight based on the total weight of the chemiluminescent system.

In some embodiments, the salicylate derivative is selected from the group consisting of: lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and cesium p-anisate. In some embodiments, the amount of the salicylate derivative ranges from 5 to 0.0005 percent by weight based on the total weight of the chemiluminescent system.

In some embodiments, the benzoate derivative is selected from the group consisting of: lithium benzoate, sodium benzoate, potassium benzoate, and cesium benzoate. In some embodiments, the amount of the benzoate derivative ranges from 5 to 0.0005 percent by weight based on the total weight of the chemiluminescent system.

In some embodiments, the at least one first solvent is selected from the group consisting of: trialkyl citrates, dialkyl phthalates, glycols, glycol ethers, and a combination thereof. In some embodiments, the amount of the at least one first solvent ranges from 15 to 90 percent by weight based on the total weight of the chemiluminescent system.

In some embodiments, the at least one peroxide is selected from the group consisting of: hydrogen peroxide, sodium peroxide, lithium peroxide, sodium perborate, sodium pyrophosphate peroxide, urea peroxide, histidine peroxide, t-butyl-hydroperoxide, peroxybenzoic acid, and sodium percarbonate. In some embodiments, the amount of the at least one peroxide ranges from 1.5 to 12 percent by weight based on the total weight of the chemiluminescent system.

In some embodiments, the at least one second solvent (e.g., bridging solvent) is selected from the group consisting of tert-butanol, 3-methyl-3-pentanol, 2-methyl-2-butanol, ethyl 2-hydroxyisobutyrate, alkyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, and propylene glycol dimethyl ether. In some embodiments, the amount of the at least one second solvent ranges from 15 to 90 percent by weight based on the total weight of the chemiluminescent system.

In some embodiments of the instant invention, the instant invention further provides a third solvent, where the third solvent is selected from the group consisting of: tert-butanol, 3-methyl-3-pentanol, 2-methyl-2-butanol, ethyl 2-hydroxyisobutyrate, methyl 2-hydroxyisobutyrate, alkyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, propylene glycol dimethyl ether, and a combination thereof. In some embodiments, the amount of the third solvent ranges from 15 to 90 percent by weight based on the total weight of the chemiluminescent system.

In some embodiments, the instant invention provides a chemiluminescent system, including: an activator system, including: (a) at least one first catalyst including at least one benzyl amine; (b) at least one second catalyst including at least one of: (i) a salicylate derivative, and (ii) a benzoate derivative; and where the chemiluminescent system is configured to exceed an expected illuminescence produced when a combination of at least one first catalyst and at least one second catalyst is utilized.

BRIEF DESCRIPTION OF THE DRAWINGS

The present invention will be further explained with reference to the attached figures. The figures constitute a part of this specification and include illustrative embodiments of the present invention and illustrate various objects and features thereof. The figures shown are not necessarily to scale, with emphasis instead generally being placed upon illustrating the principles of the present invention. Further, some features may be exaggerated to show details of particular components.

Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the term "activation" and variations thereof, as used herein, means that the oxalate system (e.g., containing at least one suitable oxalate ester with at least one dye in a suitable solvent with or without other components known to one skilled in the art) and the activator system of the present invention have been sufficiently combined such as by mixing to provide useable light.

In some embodiments, the present invention relates to a mixed catalyst system for an oxalate ester chemiluminescent system. In some embodiments, the combination of two catalysts in a chemiluminescent system would be expected to yield an average of each catalyst's performance profile.

In some embodiments, the present invention relates to a chemiluminescent system that includes an activator system and an oxalate system, where the activator system includes at least two different catalysts, where a first catalyst includes a benzyl amine and a second catalyst includes a salicylate or benzoate derivative, and where the activator system includes a first solvent, a peroxide, and a second solvent.

In some embodiments, the benzyl amine is selected from the group consisting of dialkylbenzyl amines including, but not restricted to, dimethylbenzylamine, N,N-dimethyl-1-phenylethylamine, N-ethyl-N-methylbenzylamine, diethylbenzylamine, N-methyl-N-propylbenzylamine, N,N-dibutylbenzylamine, and N,N-bis(1-methylethyl)benzenemethanamine.

In some embodiments, the benzyl amine is present in a concentration ranging from 10 percent to 0.001 percent of the total weight of the combined activator system and oxalate system.

In some embodiments, the benzyl amine is selected from the group consisting of alkyldibenzyl amines including, but not restricted to, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, and hexyl dibenzylamine.

In some embodiments, the benzyl amine is present in a concentration ranging from 10 percent to 0.001 percent of the total weight of the combined activator system and oxalate system.

In some embodiments, the benzyl amine selected from the group consisting of tribenzyl amines; tribenzyl amine, 4-methyl-N,N-bis[(4-methylphenyl)methyl]benzenemethanamine, and 4-methyl-N,N-bis(phenylmethyl)benzenemethanamine.

In some embodiments, the benzyl amine is present in a concentration ranging from 10 percent to 0.001 percent of the total weight of the combined activator system and oxalate system.

In some embodiments, the benzyl amine is selected from the group consisting of alkylarylbenzyl amines, N-methyl-N-phenylbenzenemethanamine, N-ethyl-N-phenylbenzenemethanamine, N,4-dimethyl-N-phenylbenzenemethanamine, and N-propyl-N-phenylbenzenemethanamine.

In some embodiments, the benzyl amine is present in a concentration ranging from 10 percent to 0.001 percent of the total weight of the combined activator system and oxalate system.

In some embodiments, the benzyl amine is selected from the group consisting of diarylbenzyl amines; N,N-diphenylbenzenemethanamine, and N,N-bis(4-methylphenyl)benzenemethanamine.

In some embodiments, the benzyl amine is present in a concentration ranging from 10 percent to 0.001 percent of the total weight of the combined activator system and oxalate system.

In some embodiments, the benzoate derivative is selected from the group consisting of lithium benzoate, sodium benzoate, potassium benzoate, and cesium benzoate.

In some embodiments, the benzoate derivative is present in a concentration ranging from 5 percent to 0.0005 percent of the total weight of the combined activator system and oxalate system.

In some embodiments, the salicylate derivative is selected from the group consisting of lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and cesium p-anisate.

In some embodiments, the catalysts are dissolved in a first solvent selected from the group consisting of trialkyl citrates, dialkyl phthalates, glycols, and glycol ethers.

In some embodiments, the at least one peroxide is selected from the group consisting of hydrogen peroxide, sodium peroxide, lithium peroxide, sodium perborate, sodium pyrophosphate peroxide, urea peroxide, histidine peroxide, t-butyl-hydroperoxide, peroxybenzoic acid, and sodium percarbonate.

In some embodiments, the at least one peroxide is present in a concentration ranging from 1.5 percent to 12 percent of the total weight of the combined activator system and oxalate system.

In some embodiment, the catalysts are dissolved in a second solvent configured to allow sufficient mixing of the at least one peroxide, where the second solvent is selected from the group consisting of tert-butanol, 3-methyl-3-pentanol, 2-methyl-2-butanol, ethyl 2-hydroxyisobutyrate, alkyl 2-hydroxyisobutyrate, and methyl 2-hydroxyisobutyrate; glycols; ethylene glycol and propylene glycol; and glycol ethers; ethylene glycol monomethyl ether, ethylene glycol diethyl ether, ethylene glycol monobutyl ether, ethylene glycol dibutyl ether, and propylene glycol dimethyl ether.

In some embodiments, the first solvent is present in a concentration ranging from 0 percent to 90 percent of the total weight of the combined activator system and oxalate system. In some embodiments, the first solvent is present in an amount ranging from 10 percent to 97 percent of the total weight of the combined activator system and oxalate system.

In some embodiments, the second solvent is present in a concentration ranging from 0 percent to 90 percent of the total weight of the combined activator system and oxalate system. In some embodiments, the second solvent is present in an amount ranging from 10 percent to 97 percent of the total weight of the combined activator system and oxalate system.

In some embodiments, the mixed catalyst activator system of the present invention in configured to generate the useable light having output characteristics as described herein.

In some embodiments, the system and method of the present invention may include, but are not limited to, at least one activator system combined with at least one oxalate system. Combining may include any suitable method of contacting one system with another system such as by mixing or equivalent. In some embodiments, the oxalate system may include, but is not limited to, an oxalate solution with at least one oxalate ester, at least one dye such as a fluorescer, and at least one solvent. In some embodiments, the activator system may include, but is not limited to, a catalytic system comprising at least two different catalysts, at least one first part comprising a benzyl amine and at least one second part comprising a salicylate (or benzoate) derivative; at least one solvent; a peroxide; and a bridging solvent, if necessary.

In some embodiments, the ratio of the weight of the oxalate system to the weight of the activator system ranges from 1:9 to 4:1. In some embodiments, the ratio of the weight of the oxalate system to the weight of the activator system ranges from 1:5 to 2:1. In some embodiments, the ratio of the weight of the oxalate system to the weight of the activator system ranges from 1:1 to 3:1. In some embodiments, the ratio of the weight of the oxalate system to the weight of the activator system ranges from 1:3 to 3:1. In some embodiments, the ratio of the weight of the oxalate system to the weight of the activator system ranges from 1:2 to 2:1. In some embodiments, the ratio of the weight of the oxalate system to the weight of the activator system ranges from 2:1 to 4:1. In some embodiments, the ratio of the weight of the oxalate system to the weight of the activator system ranges from 1:6 to 2:1. In some embodiments, the ratio of the weight of the oxalate system to the weight of the activator system ranges from 1:1 to 4:1.

In some embodiments, the ratio of the weight of the oxalate system to the weight of the activator system is 1:2. In some embodiments, the ratio of the weight of the oxalate system to the weight of the activator system is 2:1. In some embodiments, the ratio of the weight of the oxalate system to the weight of the activator system is 3:1. In some embodiments, the ratio of the weight of the oxalate system to the weight of the activator system is 1:8. In some embodiments, the ratio of the weight of the oxalate system to the weight of the activator system is 1:9. In some embodiments, the ratio of the weight of the oxalate system to the weight of the activator system is 4:1. In some embodiments, the ratio of the weight of the oxalate system to the weight of the activator system is 8:2. In some embodiments, the ratio of the weight of the oxalate system to the weight of the activator system is 1:5. In some embodiments, the ratio of the weight of the oxalate system to the weight of the activator system is 1:3.

In some embodiments, the benzyl amine may include, but is not limited to, dialkylbenzyl amines including, but not restricted to, dimethylbenzylamine, N,N-dimethyl-1-phenylethylamine, N-ethyl-N-methylbenzyl amine, diethylbenzylamine, N-methyl-N-propylbenzylamine, N,N-dibutylbenzylamine, and/or N,N-bis(1-methylethyl)benzenemethanamine; alkyldibenzyl amines including, but not restricted to, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, and/or hexyl dibenzylamine; and/or tribenzyl amines including, but not restricted to tribenzyl amine, 4-methyl-N,N-bis[(4-methylphenyl)methyl]benzenemethanamine, and 4-methyl-N,N-bis(phenylmethyl)benzenemethanamine; alkylarylbenzyl amines including, but not restricted to, N-methyl-N-phenylbenzenemethanamine, N-ethyl-N-phenylbenzenemethanamine, N,4-dimethyl-N-phenylbenzenemethanamine, and/or N-propyl-N-phenylbenzenemethanamine;

In some embodiments, the benzyl amine is present in a concentration ranging from 10 percent to 0.001 percent by weight, based on the total weight of the combined activator system and oxalate system. In some embodiments, the benzyl amine is present in a concentration ranging from 5 percent to 0.001 percent by weight, based on the total weight of the combined activator system and oxalate system. In some embodiments, the benzyl amine is present in a concentration ranging from 1 percent to 0.001 percent by weight, based on the total weight of the combined activator system and oxalate system.

In some embodiments, the benzyl amine is present in a concentration ranging from 5 percent to 0.1 percent by weight, based on the total weight of the combined activator system and oxalate system. In some embodiments, the benzyl amine is present in a concentration ranging from 2 percent to 1 percent by weight, based on the total weight of the combined activator system and oxalate system. In some embodiments, the benzyl amine is present in a concentration ranging from 10 percent to 3 percent by weight, based on the total weight of the combined activator system and oxalate system. In some embodiments, the benzyl amine is present in a concentration ranging from 5 percent to 1 percent by weight, based on the total weight of the combined activator system and oxalate system. In some embodiments, the benzyl amine is present in a concentration ranging from 7 percent to 2 percent by weight, based on the total weight of the combined activator system and oxalate system.

In some embodiments, the benzyl amine is present at 10 percent by weight, based on the total weight of the combined activator system and oxalate system. In some embodiments, the benzyl amine is present at 7 percent by weight, based on the total weight of the combined activator system and oxalate system. In some embodiments, the benzyl amine is present at 5 percent by weight, based on the total weight of the combined activator system and oxalate system. In some embodiments, the benzyl amine is present at 2 percent by weight, based on the total weight of the combined activator system and oxalate system. In some embodiments, the benzyl amine is present at 1 percent by weight, based on the total weight of the combined activator system and oxalate system. In some embodiments, the benzyl amine is present at 0.1 percent by weight, based on the total weight of the combined activator system and oxalate system. In some embodiments, the benzyl amine is present at 0.001 percent by weight, based on the total weight of the combined activator system and oxalate system.

In some embodiments, the benzyl amine is present at the weight percents and the weight percent ranges detailed above, based on the weight of the activator system.

In some embodiments, the benzoate derivative is chosen from a group including, but not restricted to, lithium benzoate, sodium benzoate, potassium benzoate, and cesium benzoate.

In some embodiments, the benzoate derivative is present at a concentration ranging from 5% to 0.0005% by weight, based on the total weight of the combined activator system and oxalate system. In some embodiments, the benzoate derivative is present at a concentration ranging from 2% to 0.1% by weight, based on the total weight of the combined activator system and oxalate system. In some embodiments, the benzoate derivative is present at a concentration ranging from 1% to 0.0005% by weight, based on the total weight of the combined activator system and oxalate system. In some embodiments, the benzoate derivative is present at a concentration ranging from 5% to 2% by weight, based on the total weight of the combined activator system and oxalate system. In some embodiments, the benzoate derivative is present at a concentration ranging from 0.7% to 0.0005% by weight, based on the total weight of the combined activator system and oxalate system. In some embodiments, the benzoate derivative is present at a concentration ranging from 0.5% to 0.05% by weight, based on the total weight of the combined activator system and oxalate system. In some embodiments, the benzoate derivative is present at a concentration ranging from 5% to 3% by weight, based on the total weight of the combined activator system and oxalate system.

In some embodiments, the benzoate derivative is present at 5% by weight, based on the total weight of the combined activator system and oxalate system. In some embodiments, the benzoate derivative is present at 0.5% by weight, based on the total weight of the combined activator system and oxalate system. In some embodiments, the benzoate derivative is present at 0.05% by weight, based on the total weight of the combined activator system and oxalate system. In some embodiments, the benzoate derivative is present at 0.005% by weight, based on the total weight of the combined activator system and oxalate system. In some embodiments, the benzoate derivative is present at 0.0005% by weight, based on the total weight of the combined activator system and oxalate system. In some embodiments, the benzoate derivative is present at 2% by weight, based on the total weight of the combined activator system and oxalate system. In some embodiments, the benzoate derivative is present at 3% by weight, based on the total weight of the combined activator system and oxalate system.

In some embodiments, the benzoate derivative is present at the weight percents and the weight percent ranges detailed above, based on the weight of the activator system.

In some embodiments, salicylate derivative is chosen from a group including, but not restricted to, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and/or cesium p-anisate.

In some embodiments, the salicylate derivative is present at a concentration ranging from 5% to 0.0005% by weight, based on the total weight of the combined activator system and oxalate system. In some embodiments, the salicylate derivative is present at a concentration ranging from 2% to 0.1% by weight, based on the total weight of the combined activator system and oxalate system. In some embodiments, the salicylate derivative is present at a concentration ranging from 1% to 0.0005% by weight, based on the total weight of the combined activator system and oxalate system. In some embodiments, the salicylate derivative is present at a concentration ranging from 5% to 2% by weight, based on the total weight of the combined activator system and oxalate system. In some embodiments, the salicylate derivative is present at a concentration ranging from 0.7% to 0.0005% by weight, based on the total weight of the combined activator system and oxalate system. In some embodiments, the salicylate derivative is present at a concentration ranging from 0.5% to 0.05% by weight, based on the total weight of the combined activator system and oxalate system. In some embodiments, the salicylate derivative is present at a concentration ranging from 5% to 3% by weight, based on the total weight of the combined activator system and oxalate system.

In some embodiments, the salicylate derivative is present at 5% by weight, based on the total weight of the combined activator system and oxalate system. In some embodiments, the salicylate derivative is present at 0.5% by weight, based on the total weight of the combined activator system and oxalate system. In some embodiments, the salicylate derivative is present at 0.05% by weight, based on the total weight of the combined activator system and oxalate system. In some embodiments, the salicylate derivative is present at 0.005% by weight, based on the total weight of the combined activator system and oxalate system. In some embodiments, the salicylate derivative is present at 0.0005% by weight, based on the total weight of the combined activator system and oxalate system. In some embodiments, the salicylate derivative is present at 2% by weight, based on the total weight of the combined activator system and oxalate system. In some embodiments, the salicylate derivative is present at 3% by weight, based on the total weight of the combined activator system and oxalate system.

In some embodiments, the salicylate derivative is present at the weight percents and the weight percent ranges detailed above, based on the weight of the activator system.

In some embodiments, the at least one solvent for the activator system may include, but is not limited to, trialkyl citrates, dialkyl phthalates, glycols, glycol ethers and any combination thereof.

In some embodiments, the at least one first solvent is present in an amount ranging from 0 percent to 95 percent of the total weight of the activator system. In some embodiments, the at least one first solvent is present in an amount ranging from 10 percent to 97 percent of the total weight of the activator system. In some embodiments, the at least one first solvent is present in an amount ranging from 10 percent to 80 percent of the total weight of the activator system. In some embodiments, the at least one first solvent is present in an amount ranging from 10 percent to 60 percent of the total weight of the activator system. In some embodiments, the at least one first solvent is present in an amount ranging from 30 percent to 90 percent of the total weight of the activator system. In some embodiments, the at least one first solvent is present in an amount ranging from 15 percent to 90 percent of the total weight of the activator system. In some embodiments, the at least one first solvent is present in an amount ranging from 50 percent to 95 percent of the total weight of the activator system. In some embodiments, the at least one first solvent is present in an amount ranging from 0 percent to 10 percent of the total weight of the activator system. In some embodiments, the at least one first solvent is present in an amount ranging from 95 percent to 0 percent of the total weight of the activator system.

In some embodiments, the at least one first solvent is present at 0 percent of the total weight of the activator system. In some embodiments, the at least one first solvent is present at 20 percent of the total weight of the activator system. In some embodiments, the at least one first solvent is present at 40 percent of the total weight of the activator system. In some embodiments, the at least one first solvent is present at 60 percent of the total weight of the activator system. In some embodiments, the at least one first solvent is present at 95 percent of the total weight of the activator system.

In some embodiments, the at least one second solvent is present in an amount ranging from 0 percent to 95 percent of the total weight of the activator system. In some embodiments, the at least one second solvent is present in an amount ranging from 10 percent to 97 percent of the total weight of the activator system. In some embodiments, the at least one second solvent is present in an amount ranging from 10 percent to 80 percent of the total weight of the activator system. In some embodiments, the at least one second solvent is present in an amount ranging from 10 percent to 60 percent of the total weight of the activator system. In some embodiments, the at least one second solvent is present in an amount ranging from 30 percent to 90 percent of the total weight of the activator system. In some embodiments, the at least one second solvent is present in an amount ranging from 15 percent to 90 percent of the total weight of the activator system. In some embodiments, the at least one second solvent is present in an amount ranging from 50 percent to 95 percent of the total weight of the activator system. In some embodiments, the at least one second solvent is present in an amount ranging from 0 percent to 10 percent of the total weight of the activator system. In some embodiments, the at least one second solvent is present in an amount ranging from 95 percent to 0 percent of the total weight of the activator system.

In some embodiments, the at least one second solvent is present at 0 percent of the total weight of the activator system. In some embodiments, the at least one second solvent is present at 20 percent of the total weight of the activator system. In some embodiments, the at least one second solvent is present at 40 percent of the total weight of the activator system. In some embodiments, the at least one second solvent is present at 60 percent of the total weight of the activator system. In some embodiments, the at least one second solvent is present at 95 percent of the total weight of the activator system.

In some embodiments, the at least one third solvent is present in an amount ranging from 0 percent to 95 percent of the total weight of the activator system. In some embodiments, the at least one third solvent is present in an amount ranging from 10 percent to 97 percent of the total weight of the activator system. In some embodiments, the at least one third solvent is present in an amount ranging from 10 percent to 80 percent of the total weight of the activator system. In some embodiments, the at least one third solvent is present in an amount ranging from 10 percent to 60 percent of the total weight of the activator system. In some embodiments, the at least one third solvent is present in an amount ranging from 30 percent to 90 percent of the total weight of the activator system. In some embodiments, the at least one third solvent is present in an amount ranging from 15 percent to 90 percent of the total weight of the activator system. In some embodiments, the at least one third solvent is present in an amount ranging from 50 percent to 95 percent of the total weight of the activator system. In some embodiments, the at least one third solvent is present in an amount ranging from 0 percent to 10 percent of the total weight of the activator system. In some embodiments, the at least one third solvent is present in an amount ranging from 95 percent to 0 percent of the total weight of the activator system.

In some embodiments, the at least one third solvent is present at 0 percent of the total weight of the activator system. In some embodiments, the at least one third solvent is present at 20 percent of the total weight of the activator system. In some embodiments, the at least one third solvent is present at 40 percent of the total weight of the activator system. In some embodiments, the at least one third solvent is present at 60 percent of the total weight of the activator system. In some embodiments, the at least one third solvent is present at 95 percent of the total weight of the activator system.

In some embodiments, the peroxide may include, but is not limited to, hydrogen peroxide, sodium peroxide, lithium peroxide, sodium perborate, sodium pyrophosphate peroxide, urea peroxide, histidine peroxide, t-butyl-hydroperoxide, peroxybenzoic acid, and sodium percarbonate or any combination thereof.

In some embodiments, the peroxide is present in an amount ranging from 1.5 percent to 25 percent by weight, based on the total weight of the combined activator system and oxalate system. In some embodiments, the peroxide is present in an amount ranging from 5 percent to 25 percent by weight, based on the total weight of the combined activator system and oxalate system. In some embodiments, the peroxide is present in an amount ranging from 2 percent to 20 percent by weight, based on the total weight of the combined activator system and oxalate system. In some embodiments, the peroxide is present in an amount ranging from 10 percent to 15 percent by weight, based on the total weight of the combined activator system and oxalate system. In some embodiments, the peroxide is present in an amount ranging from 1.55 percent to 5 percent by weight, based on the total weight of the combined activator system and oxalate system.

In some embodiments, the peroxide is present at 1.5 percent by weight, based on the total weight of the combined activator system and oxalate system. In some embodiments, the at least one peroxide is present at 3 percent by weight, based on the total weight of the combined activator system and oxalate system. In some embodiments, the peroxide is present at 5 percent by weight, based on the total weight of the combined activator system and oxalate system. In some embodiments, the peroxide is present at 10 percent by weight, based on the total weight of the combined activator system and oxalate system. In some embodiments, the peroxide is present at 20 percent by weight, based on the total weight of the combined activator system and oxalate system. In some embodiments, the peroxide is present at 25 percent by weight, based on the total weight of the combined activator system and oxalate system.

In some embodiments, the peroxide is present at the weight percents and the weight percent ranges detailed above, based on the weight of the activator system.

In some embodiments, the bridging solvent may include, but is not limited to, tert-butanol, 3-methyl-3-pentanol, 2-methyl-2-butanol, ethyl 2-hydroxyisobutyrate, alkyl 2-hydroxyisobutyrate and methyl 2-hydroxyisobutyrate; glycols chosen from, but not restricted to ethylene glycol and propylene glycol; and glycol ethers chosen from, but not restricted to ethylene glycol monomethyl ether, ethylene glycol diethyl ether, ethylene glycol monobutyl ether, ethylene glycol dibutyl ether, and propylene glycol dimethyl ether or any combination thereof.

In some embodiments, the bridging solvent is present in an amount ranging from 0 percent to 95 percent of the total weight of the activator system. In some embodiments, the bridging solvent is present in an amount ranging from 10 percent to 80 percent of the total weight of the activator system. In some embodiments, the bridging solvent is present in an amount ranging from 10 percent to 60 percent of the total weight of the activator system. In some embodiments, the bridging solvent is present in an amount ranging from 30 percent to 90 percent of the total weight of the activator system. In some embodiments, the bridging solvent is present in an amount ranging from 15 percent to 90 percent of the total weight of the activator system. In some embodiments, the bridging solvent is present in an amount ranging from 50 percent to 95 percent of the total weight of the activator system. In some embodiments, the bridging solvent is present in an amount ranging from 0 percent to 10 percent of the total weight of the activator system.

In some embodiments, the bridging solvent is present at 0 percent of the total weight of the activator system. In some embodiments, the bridging solvent is present at 20 percent of the total weight of the activator system. In some embodiments, the bridging solvent is present at 40 percent of the total weight of the activator system. In some embodiments, the bridging solvent is present at 60 percent of the total weight of the activator system. In some embodiments, the bridging solvent is present at 95 percent of the total weight of the activator system.

Non-Limiting Examples

Figure 1:
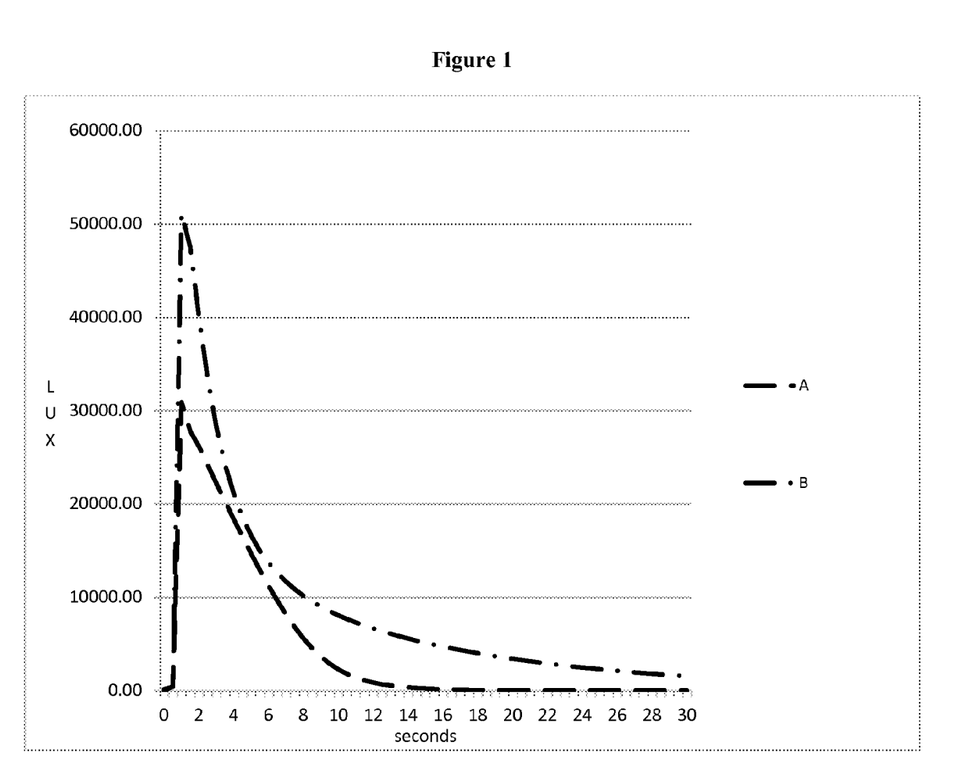
FIG. 1 illustrates aspects of some embodiments of the instant invention.

FIG. 1 represents the chemical light output at room temperature of a standard oxalate ester system having a rubrene fluorescer (dye) and an activator system containing 0.2 percent of sodium salicylate in triethyl citrate (TEC) with 2.3 percent peroxide content using 50 percent aqueous hydrogen peroxide (A) and the chemical light output at room temperature of a standard oxalate ester system with rubrene fluorescer (dye) and an activator system containing 0.2 percent of tribenzyl amine in triethyl citrate (TEC) with 2.3 percent peroxide content using 50 percent aqueous hydrogen peroxide (B).

Figure 2:
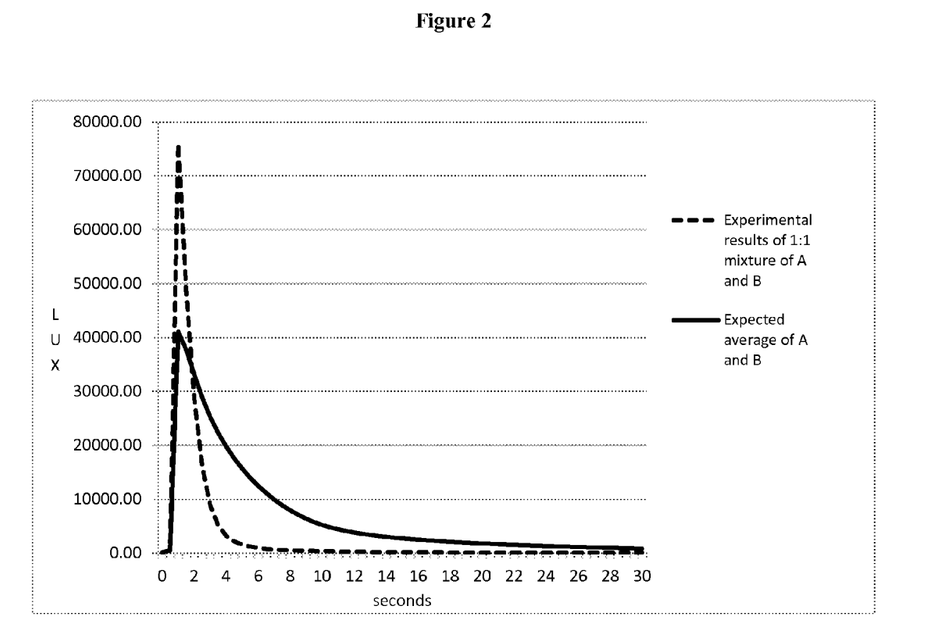
FIG. 2 illustrates further aspects of some embodiments of the instant invention.

FIG. 2 represents the chemical light output at room temperature of the average of the two results in FIG. 1 and the chemical light output of a standard oxalate ester system with rubrene fluorescer (dye) and an activator system containing a 1:1 mixture of A and B shown in FIG. 1 such that the total amount of catalyst is unchanged.

Figure 3:
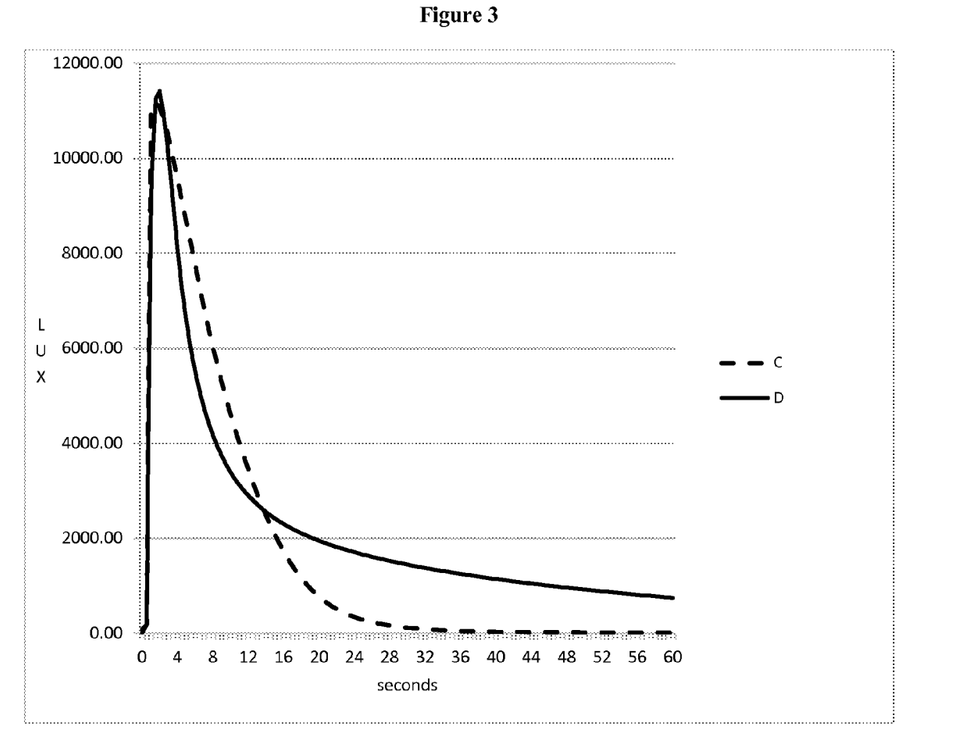
FIG. 3 illustrates yet further aspects of some embodiments of the instant invention.

FIG. 3 represents the chemical light output at room temperature of a standard oxalate ester system with rubrene fluorescer (dye) and an activator system containing 0.1 percent of sodium salicylate in triethyl citrate (TEC) with 2.3 percent peroxide content using 70 percent aqueous hydrogen peroxide (C) and the chemical light output at room temperature of a standard oxalate system with rubrene fluorescer (dye) and an activator system containing 0.1 g of tribenzyl amine in triethyl citrate (TEC) with 2.3 percent peroxide content using 70 percent aqueous hydrogen peroxide (D).

Figure 4:
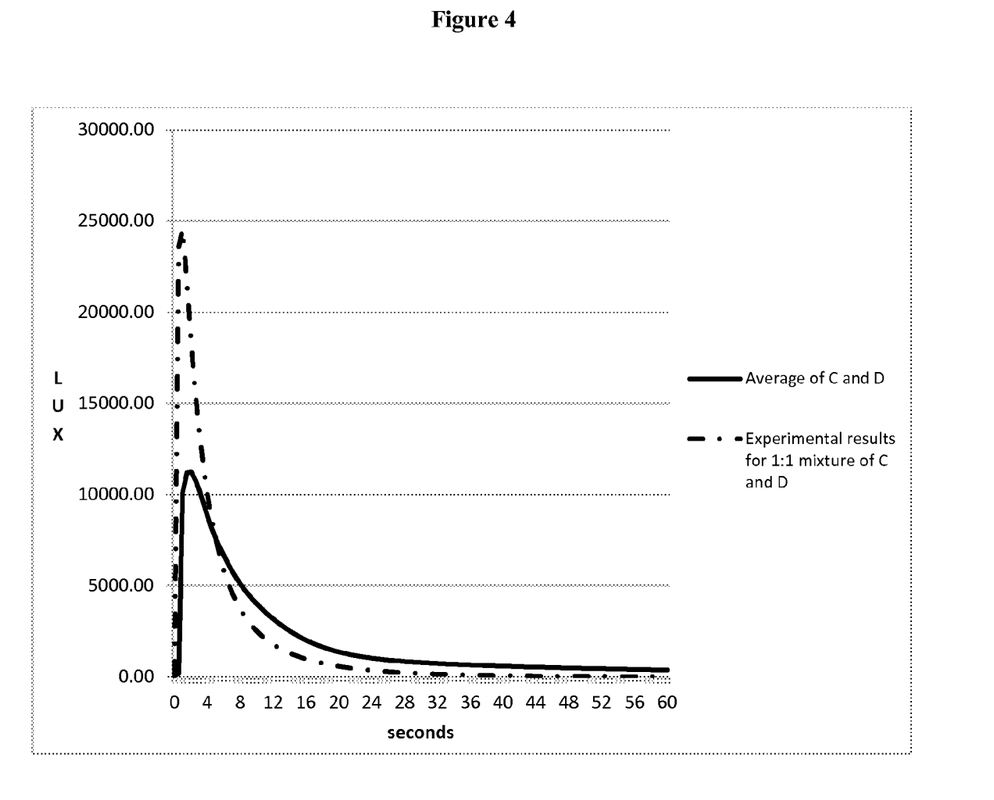
FIG. 4 illustrates yet further aspects of some embodiments of the instant invention.

FIG. 4 represents the chemical light output at room temperature of the average of the two results in FIG. 3 and the chemical light output of a standard oxalate ester system with rubrene fluorescer (dye) and an activator system containing a 1:1 mixture of C and D shown in FIG. 3 such that the total amount of catalyst is unchanged. The tests were conducted measuring the light output with an ILT 1700 light meter.

In some embodiments, the instant invention provides a chemiluminescent system, including: an activator system, including: (a) at least one first catalyst including at least one benzyl amine; (b) at least one second catalyst including at least one of: (i) a salicylate derivative, and (ii) a benzoate derivative; (c) at least one first solvent, and (d) at least one peroxide, where the at least one first catalyst is present in an amount ranging from 1 to 99 percent by weight of a combination of the at least one first catalyst and the at least one second catalyst; where the at least one second catalyst is present in an amount ranging from 99 to 1 percent by weight of the combination of the at least one first catalyst and the at least one second catalyst; where a total concentration of the combination ranges from 0.002 to 25 percent by weight based on a total weight of the activator system; and where the chemiluminescent system has at least one chemiluminescent property.

In some embodiments, the instant invention further provides an oxalate system, providing: (a) at least one oxalate ester, (b) at least one second solvent, (c) at least one fluorescer, and (d) at least one inorganic salt, where a ratio of a weight of the oxalate system to a weight of the activator system ranges from 1:9 to 4:1.

In some embodiments, the at least one benzyl amine is selected from the group consisting of: dialkylbenzyl amines, alkyldibenzyl amines, tribenzyl amines, alkylarylbenzyl amines, and diarylbenzyl amines. In some embodiments, the amount of the at least one benzyl amine ranges from 10 to 0.001 percent by weight based on the total weight of the chemiluminescent system.

In some embodiments, the salicylate derivative is selected from the group consisting of: lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and cesium p-anisate. In some embodiments, the amount of the salicylate derivative ranges from 5 to 0.0005 percent by weight based on the total weight of the chemiluminescent system.

In some embodiments, the benzoate derivative is selected from the group consisting of: lithium benzoate, sodium benzoate, potassium benzoate, and cesium benzoate. In some embodiments, the amount of the benzoate derivative ranges from 5 to 0.0005 percent by weight based on the total weight of the chemiluminescent system.

In some embodiments, the at least one first solvent is selected from the group consisting of: trialkyl citrates, dialkyl phthalates, glycols, glycol ethers, and a combination thereof. In some embodiments, the amount of the at least one first solvent ranges from 15 to 90 percent by weight based on the total weight of the chemiluminescent system.

In some embodiments, the at least one peroxide is selected from the group consisting of: hydrogen peroxide, sodium peroxide, lithium peroxide, sodium perborate, sodium pyrophosphate peroxide, urea peroxide, histidine peroxide, t-butyl-hydroperoxide, peroxybenzoic acid, and sodium percarbonate. In some embodiments, the amount of the at least one peroxide ranges from 1.5 to 12 percent by weight based on the total weight of the chemiluminescent system.

In some embodiments, the at least one second solvent (e.g., bridging solvent) is selected from the group consisting of tert-butanol, 3-methyl-3-pentanol, 2-methyl-2-butanol, ethyl 2-hydroxyisobutyrate, alkyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, and propylene glycol dimethyl ether. In some embodiments, the amount of the at least one second solvent ranges from 15 to 90 percent by weight based on the total weight of the chemiluminescent system.

In some embodiments of the instant invention, the instant invention further provides a third solvent, where the third solvent is selected from the group consisting of: tert-butanol, 3-methyl-3-pentanol, 2-methyl-2-butanol, ethyl 2-hydroxyisobutyrate, methyl 2-hydroxyisobutyrate, alkyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, propylene glycol dimethyl ether, and a combination thereof. In some embodiments, the amount of the third solvent ranges from 15 to 90 percent by weight based on the total weight of the chemiluminescent system.

In some embodiments, the instant invention provides a chemiluminescent system, including: an activator system, including: (a) at least one first catalyst including at least one benzyl amine; (b) at least one second catalyst including at least one of: (i) a salicylate derivative, and (ii) a benzoate derivative; and where the chemiluminescent system is configured to exceed an expected illuminescence produced when a combination of at least one first catalyst and at least one second catalyst is utilized.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A chemiluminescent system, comprising:
    an activator system, comprising:
        (a) at least one first catalyst comprising at least one benzyl amine;
        (b) at least one second catalyst comprising at least one of:
            (i) a salicylate derivative, and
            (ii) a benzoate derivative;
        (c) at least one first solvent, and
        (d) at least one peroxide,
    wherein the at least one first catalyst is present in an amount ranging from 1 to 99 percent by weight of a combination of the at least one first catalyst and the at least one second catalyst;
    wherein the at least one second catalyst is present in an amount ranging from 99 to 1 percent by weight of the combination of the at least one first catalyst and the at least one second catalyst;
    wherein a total concentration of the combination ranges from 0.002 to 25 percent by weight based on a total weight of the activator system; and
    wherein the chemiluminescent system has at least one chemiluminescent property.

2. The chemiluminescent system of claim 1, further comprising:
    an oxalate system, comprising:
        (a) at least one oxalate ester,
        (b) at least one second solvent,
        (c) at least one fluorescer, and
        (d) at least one inorganic salt,
    wherein a ratio of a weight of the oxalate system to a weight of the activator system ranges from 1:9 to 4:1.

3. The chemiluminescent system of claim 1, wherein the at least one benzyl amine is selected from the group consisting of: dialkylbenzyl amines, alkyldibenzyl amines, tribenzyl amines, alkylarylbenzyl amines, and diarylbenzyl amines.

4. The chemiluminescent system of claim 1, wherein the amount of the at least one benzyl amine ranges from 10 to 0.001 percent by weight based on the total weight of the chemiluminescent system.

5. The chemiluminescent system of claim 1, wherein the salicylate derivative is selected from the group consisting of: lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and cesium p-anisate.

6. The chemiluminescent system of claim 1, wherein the amount of the salicylate derivative ranges from 5 to 0.0005 percent by weight based on the total weight of the chemiluminescent system.

7. The chemiluminescent system of claim 1, wherein the benzoate derivative is selected from the group consisting of: lithium benzoate, sodium benzoate, potassium benzoate, and cesium benzoate.

8. The chemiluminescent system of claim 1, wherein the amount of the benzoate derivative ranges from 5 to 0.0005 percent by weight based on the total weight of the chemiluminescent system.

9. The chemiluminescent system of claim 1, wherein the at least one first solvent is selected from the group consisting of: trialkyl citrates, dialkyl phthalates, glycols, glycol ethers, and a combination thereof.

10. The chemiluminescent system of claim 1, wherein the amount of the at least one first solvent ranges from 15 to 90 percent by weight based on the total weight of the chemiluminescent system.

11. The chemiluminescent system of claim 1, wherein the at least one peroxide is selected from the group consisting of: hydrogen peroxide, sodium peroxide, lithium peroxide, sodium perborate, sodium pyrophosphate peroxide, urea peroxide, histidine peroxide, t-butyl-hydroperoxide, peroxybenzoic acid, and sodium percarbonate.

12. The chemiluminescent system of claim 1, wherein the amount of the at least one peroxide ranges from 1.5 to 12 percent by weight based on the total weight of the chemiluminescent system.

13. The chemiluminescent system of claim 2, wherein the at least one second solvent is selected from the group consisting of tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, and propylene glycol dimethyl ether.

14. The chemiluminescent system of claim 2, wherein the amount of the at least one second solvent ranges from 15 to 90 percent by weight based on the total weight of the chemiluminescent system.

15. The chemiluminescent system of claim 1, further comprising: a third solvent, wherein the third solvent is selected from the group consisting of: tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, propylene glycol dimethyl ether, and a combination thereof.

16. The chemiluminescent system of claim 15, wherein the amount of the third solvent ranges from 15 to 90 percent by weight based on the total weight of the chemiluminescent system.

* * * * *